United States Patent [19]

Sekiyama et al.

[11] 3,960,939

[45] June 1, 1976

[54] METHOD FOR PREPARING SORBIC ACID

[75] Inventors: Kunihiko Sekiyama, Kashihara; Yasuyoshi Taga, Ogaki; Shigemi Fujita, Kaizu, all of Japan

[73] Assignee: Nippon Gohsei Kagaku Kabushiki Kaisha, Osaka, Japan

[22] Filed: June 3, 1975

[21] Appl. No.: 583,270

[52] U.S. Cl. ............................................. 260/526 N
[51] Int. Cl.² ........................................ C07C 51/00
[58] Field of Search ............................... 260/526 N

[56] References Cited
FOREIGN PATENTS OR APPLICATIONS

| | | | |
|---|---|---|---|
| 1,059,899 | 6/1959 | Germany | 260/526 N |
| 989,798 | 4/1965 | United Kingdom | 260/526 N |

*Primary Examiner*—Vivian Garner
*Attorney, Agent, or Firm*—Armstrong, Nikaido & Wegner

[57] ABSTRACT

Method for preparing sorbic acid comprising the steps of uniformly dispersing the polyester, prepared by the reaction of crotonaldehyde with ketene, and hydrochloric acid into a saturated aliphatic hydrocarbon having a boiling point at atmospheric pressure of 150° to 260°C., heating the dispersed reaction mixture at 80° to 135°C. to convert the polyester to sorbic acid, separating the resulting reaction mixture into two layers, evaporating sorbic acid together with hydrocarbon from the upper layer by centrifugal thin film type evaporator under conditions of 20 to 40 mmHg in absolute pressure and of 140° to 160°C., and recovering sorbic acid from the evaporated sorbic acid-hydrocarbon mixture. Sorbic acid of high quality can be obtained in high yield.

6 Claims, 1 Drawing Figure

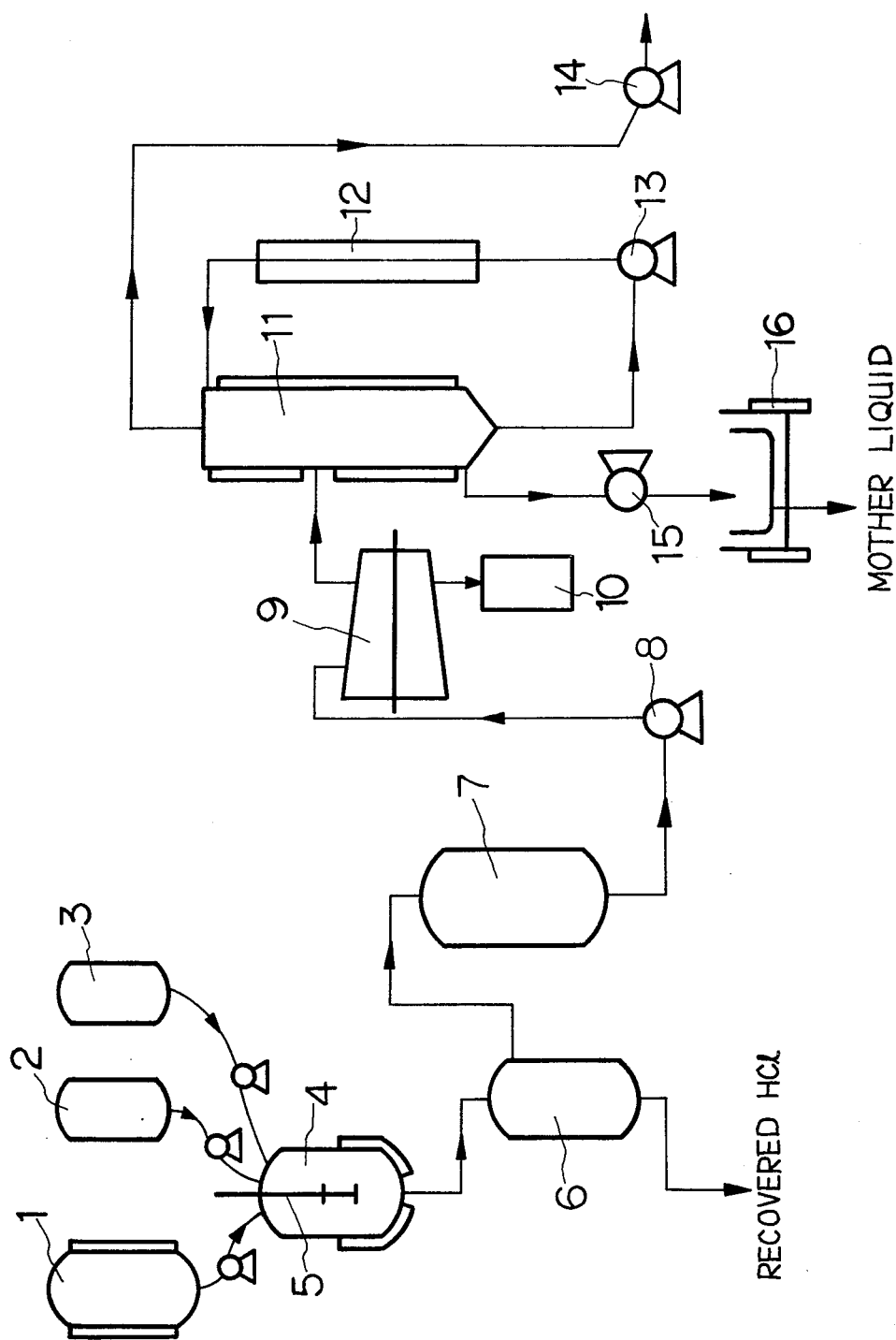

METHOD FOR PREPARING SORBIC ACID

BACKGROUND OF THE INVENTION

The present invention relates to a preparation of sorbic acid, and more particularly to a method for preparing sorbic acid of high quality in high yield.

Sorbic acid has been manufactured by reacting crotonaldehyde with ketene to form polyester and converting the polyester to sorbic acid by means of heating, or in the presence of an alkali or mineral acid. A method employing a mineral acid, especially hydrochloric acid, has been advantageously applied because the yield or the quality of obtaines sorbic acid is superior. There has been known, for instance, a method of splitting the polyester in diluted or concentrated hydrochloric acid and then recovering the sorbic acid deposited in the reaction mixture, or a method of splitting the polyester in the presence of hydrochloric acid and a water-miscible organic solvent such as acetic acid or dioxane and then recovering sorbic acid from the solvent.

However, in the case of splitting the polyester by a diluted hydrochloric acid, the yieldd of the obtained sorbic acid is at most about 85 %. In the case of employing a concentrated hydrochloric acid (around 35 % by weight), the yield reaches about 90 %. But, in such a method by-production of a colored resinous substance is inevitable during the reaction and, therefore, the method requires the particular purification step to remove the colored resinous substance. Such a contamination deteriorates the quality of sorbic acid. In order to purify the sorbic acid obtained in such a method, there has been applied recrystallization in the presence of active carbon. This complicates the process steps and the loss of sorbic acid due to adsorption on active carbon is considerable.

In the case of splitting the polyester in a water-miscible organic solvent, the reaction proceeds homogeneously and the obtained sorbic acid is relatively good in quality. However, the method requires a procedure such as distillation to remove a large quantity of the solvent or addition of a non-solvent, e.g. water, to the reaction mixture, because the formed sorbic acid is dissolved in the solvent in large quantities. Moreover, the method has a considerable difficulty in recovering the hydrochloric acid employed.

For the purpose of overcoming the defects in a conventional method as mentioned above, the present inventors have proposed a method for preparing sorbic acid which consists of the steps of uniformly dispersing the polyester and a small quantity of hydrochloric acid into a saturated aliphatic hydrocarbon having a boiling point at atmospheric pressure of 90° to 180°C., heating the dispersed reaction mixture at a temperature of 80° to 135°C., and recovering the sorbic acid precipitated by cooling the reaction mixture. This method has the advantages that the amount of hydrochloric acid is less than that in a conventional method, and that sorbic acid is produced in high yield. However, a colored resinous substance is dissolved in the hydrocarbon solution of sorbic acid and the sorbic acid precipitated from such a solution is also colored. Therefore, this method is not still satisfactory.

OBJECTS OF THE INVENTION

It is an object of the present invention to provide an improved method for preparing sorbic acid.

A further object of the invention is to provide a method for preparing sorbic acid of high quality in high yield.

These and other objects of the invention will become apparent from the description hereinafter.

BRIEF DESCRIPTION OF THE DRAWING

The accompanying drawing is a flow sheet showing an embodiment for practicing the present invention.

DETAILED DESCRIPTION

It has now been found that the above-mentioned objects can be accomplished by uniformly dispersing the polyester and a small quantity of hydrochloric acid into a saturated aliphatic hydrocarbon having a boiling point at atmospheric pressure of 150° to 260°C., heating the dispersed reaction mixture at a temperature of 80° to 135°C., allowing to stand the reaction mixture to separate into two layers, i.e. an upper layer being hydrocarbon solution of sorbic acid and an under layer containing hydrochloric acid, evaporating sorbic acid together with hydrocarbon from the upper layer by a centrifugal thin film type evaporator, condensing an evaporated mixed vapor of sorbic acid and hydrocarbon, and recovering sorbic acid from the resulting mixture.

According to the present invention, white, purified sorbic acid can be obtained in high yield.

The specific saturated aliphatic hydrocarbons do not dissolve, or scarcely dissolve the polyester and hydrochloric acid at a reaction temperature, and on the other hand, readily dissolve sorbic acid. The hydrocarbons differ from an aromatic hydrocarbon, that dissolves both polyester and hydrochloric acid, such as benzene, toluene or xylene employed in a conventional method. The specific saturated aliphatic hydrocarbons have an advantage over aromatic hydrocarbons in being harmless to human being, and this is important not only in safety upon operation but also in safety upon the application as a preservative for foods. The employment of the specific hydrocarbons as a reaction medium is one of the features of the present invention. When splitting of the polyester by hydrochloric acid is effected in such an aromatic hydrocarbon, lowering of per-pass yield can not be avoided since the aromatic hydrocarbon dissolves both polyester and sorbic acid even at a low temperature. When the specific solvent is employed and the polyester is split at the prescribed temperature according to the present invention, the reaction smoothly proceeds in the presence of less amount of hydrochloric acid as compared with a conventional method.

By separating the resulting reaction mixture into two layers and then subjecting the obtained upper layer being hydrocarbon solution of sorbic acid to evaporation, the colored resinous substance which contaminates sorbic acid can be completely removed. In the evaporation, a centrifugal thin film type evaporator is employed, and sorbic acid is evaporated together with the hydrocarbon. The evaporation is preferably carried out at an absolute pressure of 20 to 40 mmHg and a temperature of 140° to 160°C. It is undesirable to evaporate sorbic acid and hydrocarbon individually. For instance, when a usual evaporator or a wetted wall type evaporator is employed, the hydrocarbon first evaporates and then sorbic acid evaporates. Such a two-stage evaporation causes troubles such as blockade of evaporator. Thus, according to the present invention, the converting of the polyester to sorbic acid and the purification of sorbic acid are efficiently effected and sorbic acid of high quality can be obtained.

Examples of the saturated aliphatic hydrocarbon employed in the present invention are, for instance, 3-ethylpentane, n-nonane, iso-nonane, n-decane, iso-decane, n-undecane, and the like, but the hydrocarbons are not limited to the above listed hydrocarbons. The hydrocarbons may be, of course, employed in a form of mixture thereof. In the present invention, the hydrocarbon is generally employed in an amount of 5 to 8 parts by weight per 1 part by weight of the polyester.

The concentration of hydrochloric acid is freely selected from a range of 20 to 36 % by weight, and preferably of not less than 25 %. A small amount of hydrochloric acid suffices for splitting the polyester, and usually the hydrochloric acid is employed in a ratio of 0.05 to 0.20 part by weight of hydrogen chloride per one part by weight of the polyester. This is another feature of the present invention unlike a conventional method employing large quantities of hydrochloric acid. According to the present invention, it is also possible to form a azeotropic mixture of hydrocarbon-water-hydrogen chloride during the reaction. By forming the azeotropic mixture, there can be avoided a lowering of the concentration of hydrochloric acid due to the vaporization of hydrogen chloride and the hydrochloric acid recovered after the completion of the reaction can be directly reused in the next reaction.

It is necessary to uniformly disperse both polyester and hydrochloric acid into the hydrocarbon, because the hydrocarbons employed in the invention do not substantially dissolve them. When the dispersion is insufficient, the polyester and the formed sorbic acid agglomerate during the reaction, and as a result, the reaction may be prevented or the formed sorbic acid may further be decomposed and the yield of sorbic acid lowers. Uniform dispersion may be attained by a mechanical means such as a vigorous agitation or injection, or by other means such as ultrasonic waves. In the present invention, a small quantity of a surface active agent is suitably added to the reaction mixture in order to obtain more stable dispersion. As the surface active agent, various kinds of the agent can be employed. Examples of the suitable surface active agent are non-ionic surface active agents such as polyoxyethylene alkyl ethers having 3 to 30 mols of ethylene oxide unit or alkyl phenyl ethers, and the sulfonates thereof. The surface active agent is usually added to the reaction mixture in an amount of 0.10 to 0.20 part by weight per 100 parts by weight of the reaction mixture.

In the present invention, the heating of the dispersed reaction mixture is carried out at a temperature of 80° to 135°C. At a temperature below 80°C., the dispersion tends to become unstable since the formed sorbic acid partially precipitates or the agglomeration occurs and the viscosity of the dispersion rises. The unstable dispersion results in lowering of the yield of sorbic acid. On the other hand, the heating at a temperature over 135°C. is also undesirable since the formed sorbic acid may decompose and the yield lowers. The heating is carried out within the above temperature range, usually for 1 to 8 hours, and preferably for 2 to 4 hours.

After the completion of the reaction, the resulting reaction mixture is separated into two layers by allowing to stand, that is, the upper layer being hydrocarbon solution of sorbic acid and the under layer containing hydrochloric acid. A small quantity of the carbonized resinous materials produced during the reaction almost settles down in the under layer. The settled materials are readily removed out of the under layer by filtration. The hydrochloric acid so recovered from the under layer can be reused in the next reaction. The separated upper layer is then subjected to the evaporation directly, or after removing a trace of hydrochloric acid dissolved in the layer by washing with water or neutralization. The evaporation is carried out by a centrifugal thin film type evaporator and sorbic acid is evaporated together with the hydrocarbon from the upper layer. The evaporation is preferably carried out at an absolute pressure of 20 to 40 mmHg and a temperature of 140° to 160°C. If desired, the upper layer may be passed through a concentrator such as a wetted type or a tower to remove water prior to the evaporation. The evaporation mixed vapor of sorbic acid and the hydrocarbon is then condensed. Both sorbic acid and hydrocarbon are recovered in a form of solution or slurry, and on the other hand, colored high boiling substances are removed from the bottom of the evaporator. The solution or slurry are cooled to a temperature of 10° to 30°C. to precipitate sorbic acid. If desired, the solution or slurry may be purified with an active carbon before cooling. In the case of slurry, it is desirable to dissolve the sorbic acid by heating. The precipitated sorbic acid is then separated from the hydrocarbon in usual way such as centrifugation or filtration and is dried. The sorbic acid so recovered may be recrystallized from water or water-organic solvent system, if it is required to obtain more purified sorbic acid. The recovered hydrocarbon can be reused. A part of the recovered hydrocarbon may also be used to condense the mixed vapor of sorbic acid and hydrocarbon given off from the evaporator.

The method of the present invention is now explained by the drawing which is a flow sheet showing one instance of the present invention. From a polyester supply tank 1, a hydrochloric acid supply tank 2 and a hydrocarbon supply tank 3, the polyester, hydrochloric acid and the hydrocarbon are supplied into a reaction tank 4, and they are uniformly dispersed by a stirrer 5 and heated. After the completion of the reaction, the resulting reaction mixture is transferred into a separation tank 6. The upper hydrocarbon layer separated from the under hydrochloric acid layer is stored in a tank 7, and is continuously supplied into a centrifugal thin film type evaporator 9 by a pump 8. While the evaporation is carried out, non-volatile resinous substances are continuously taken out into a tank 10. A jacket of the evaporator is heated by a means such as steam and also the pressure in the evaporator is controlled by a vacuum pump 14. The evaporated mixed vapor of sorbic acid and hydrocarbon is condensed by a contact condenser 11 which is previously charged with the same hydrocarbon as that employed in the reaction. The hydrocarbon charged in the contact condenser 11 is circulated through a cooling apparatus 12 by a pump 13. The resulting hydrocarbon solution or slurry of sorbic acid is continuously taken out through a pump 15. From the solution or slurry so obtained, sorbic acid is recovered in usual way. For instance, the sorbic acid precipitated by cooling is separated by a centrifuge 16.

The present invention is more specifically described and explained by means of the following Examples.

EXAMPLE 1

A 100 liter reactor equipped with a homomixer was charged with 60 kg. of a mixture of isoparaffins having 9 to 11 carbon atoms (distillates of 158° to 177°C.), 5.0 kg. of 30 % hydrochloric acid in which 100 g. of a nonionic surface active agent (commercially available under the registered trademark "Emuljet-100" made by DAI-ICHI KOGYO SEIYAKU CO., LTD.) was dissolved, and 10 kg. of the polyester. At a temperature of 90°C., the isoparaffins, the hydrochloric acid and the polyester were uniformly dispersed by means of the homomixer, and reaction was carried out for 1 hour with agitation. Then the mixer was stopped, and the reaction mixture was allowed to stand at the same temperature as above to separate into the upper hydrocarbon layer andd under aqueous layer (namely hydrochloric acid layer). In order to remove the hydrochloric acid dissolved in the upper layer, the upper layer was washed with 1 kg. of hot water 2 times successively. The hydrocarbon layer so obtained was evaporated by a centrifugal thin film type evaporator in such a manner as shown in the accompanying drawing to give a slurry of sorbic acid.

That is to say, the hydrocarbon layer stored in a tank was continuously supplied to the centrifugal thin film evaporator having a heat transfer area of 0.1 m.$^2$ at a flow rate of 25 liters/hour. While the evaporation was carried out, non-volatile resinous substances were continuously taken out from the bottom of evaporator. A jacket of the evaporator was heated by steam of 2.5 kg./cm.$^2$G. and the pressure in the evaporator was controlled at an absolute pressure of 30 to 40 mmHg by a vacuum pump. The evaporated mixed vapor of sorbic acid and the isoparaffins was condensed by a contact condenser, which was previously charged with 10 kg. of the same mixture of isoparaffins as above, to give a slurry of sorbic acid. The resulting slurry was then cooled to 15°C.

The cooled slurry was charged in a centrifuge, and 9.0 kg. of a cake or sorbic acid was obtained. The cake so obtained was sufficiently mixed, and a part of the mixed cake was collected to determine a water content. The collected cake was dried, and as a result of calculating the water content on the basis of weight change, the water content of the cake was 9.9 % by weight. Therefore, the cake contained 8.1 kg. of sorbic acid. Also, in 64 kg. of the mother liquid recovered, 1.1 kg. of sorbic acid was contained. That is, the yield of sorbic acid was 92 %. The purity and melting point of the dry sorbic acid so obtained were 99.7 % and 134.5°C., respectively.

On the other hand, 2 liters of water and 2.5 g. of powdery active carbon were added to 50 g. of the above cake of sorbic acid, acid the sorbic acid was recrystallized in usual way. The sorbic acid was precipitated and recovered and further dried at a temperature of 60°C. and an absolute pressure of 100 mmHg. In 100 ml. of methanol, 10 g. of the dry sorbic acid so obtained was dissolved. The color of the methanol solution was APHA 5. The percent transmission of the methanol solution was also measured by a spectrophotometer. The percent transmissions at wave lengths of 430 m$\mu$ and 350 m$\mu$ were 99.0 % and 95.5 %, respectively.

EXAMPLE 2

The same reactor as employed in Example 1 was charged with 50 kg. of the mixture of isoparaffins recovered by the centrifugation in Example 1, which contained about 0.86 kg. of sorbic acid, 10 kg. of the same mixture of isoparaffins as employed in Example 1, 5.0 kg. of 30 % hydrochloric acid in which 100 g. of "Emuljet-100" was dissolved, and 10 kg. of the polyester, and the same procedure as in Example 1 was repeated.

The water content of the obtained cake of sorbic acid was 10.2 %, and 8.7 kg. of sorbic acid was contained in the cake. Also, in 65 kg. of the recovered mixture of isoparaffins, 1.8 kg. of sorbic acid was contained. The yield of sorbic acid was 96.4 %.

On the other hand, 2 liters of water and 2.5 g. of powdery active carbon were added to 50 g. of the above cake, and sorbic acid was recrystallized in usual way. In 100 ml. of methanol, 10 g. of the sorbic acid so recrystallized was dissolved. The color of the methanol solution was APHA 5. The percent transmission of the methanol solution as also measured by a spectrophotometer. The percent transmissions at wave lengths of 430 m$\mu$ and 350 m$\mu$ were 99.0 % and 95.0 %, respectively.

EXAMPLE 3

The splitting of the polyester was carried out in the same manner as in Example 1 except that a mixture os isoparaffins having 9 to 12 carbon atoms (distillates of 174° to 189°C.) was employed instead of the mixture of isoparaffins having 9 to 11 carbon atoms and then hydrochloric acid was removed from the obtained hydrocarbon layer. The hydrocarbon layer so obtained was subjected to evaporation by means of the same centrifugal thin film evaporator (heat transfer area: 0.1 m.$^2$) as in Example 1 under the conditions of 30 to 35 mmHg. in absolute pressure and 135°C. in temperature, and the evaporated mixed vapor of sorbic acid and the isoparaffins was condensed by a contact condenser and then cooled to 15°C. to give a slurry consisting of sorbic acid and isoparaffins. The slurry was subjected to centrifugation and 8.5 kg. of a cake of sorbic acid was obtained.

The water content of the cake so obtained was 9 % and, therefore, 7.75 kg. of sorbic acid was contained in the cake. Also, 1.1 kg. of sorbic acid was contained on 61 kg. of the recovered mixture of isoparaffins. The yield of sorbic acid was 88.5 %.

The purity and melting point of the dry sorbic acid were 99.3 % and 134°C., respectively.

On the other hand, 2 liters of a methanol-water mixed solvent (1 : 1) and 5 g. of powdery active carbon were added to 50 g. of the cake, and sorbic acid was recrystallized in usual way. The sorbic acid precipitated at 10°C. and recovered, was dried at a temperature of 60°C. and an absolute pressure of 100 mmHg. In 100 ml. of methanol, 10 g. of the dry sorbic acid so obtained was dissolved. The color of the methanol solution was APHA 5. The percent transmission of the methanol solution was also measured by a spectrophotometer. The percent transmission at wave lengths of 430 m$\mu$ and 350 m$\mu$ were 98.0 % and 92.0 %, respectively.

What we claim is:

1. In a method for preparing sorbic acid by heating a polyester prepared by the reaction of crotonaldehyde with ketene, in a reaction medium in the presence of hydrochloric acid to convert the polyester to sorbic acid and then recovering the sorbic acid from the reaction mixture, the improvement which comprises the steps of a. dispersing the polyester and hydrochloric acid into a saturated aliphatic hydrocarbon having a boiling point at atmospheric pressure of 150° to 260°C., b. heating the dispersed reaction mixture at a temperature of 80° to 135°C. to convert the polyester to sorbic acid, c. allowing the reaction mixture to separate into an upper layer being hydrocarbon solution of sorbic acid and an under layer containing hydrochloric acid, d. evaporating sorbic acid together with the hydrocarbon from the upper layer by a centrifugal thin film type evaporator, and e. recovering sorbic acid from the evaporated sorbic acid-hydrocarbon mixture.

2. The method of claim 1, wherein said evaporation is carried out by means of a centrifugal thin film type evaporator at an absolute pressure of 20 to 40 mmHg and a temperature of 140° to 160°C.

3. The method of claim 1, wherein said saturated aliphatic hydrocarbon is at least one member selected from the group consisting of 3-ethylpentane, n-nonane, iso-nonane, n-decane, iso-decane and n-undecane.

4. The method of claim 1, wherein said saturated aliphatic hydrocarbon is employed in an amount of 5 to 8 parts by weight per 1 part by weight of the polyester.

5. The method of claim 1, wherein said hydrochloric acid is employed in a ratio of 0.05 to 0.20 part by weight of hydrogen chloride per 1 part by weight of the polyester.

6. The method of claim 1, in which a non-ionic surface active agent is employed as a dispersing agent in an amount of 0.01 to 0.20 part by weight per 100 parts by weight of the reaction mixture.

* * * * *